United States Patent [19]

Kawanabe et al.

[11] Patent Number: 4,665,874
[45] Date of Patent: May 19, 1987

[54] DEVICE FOR SENSING AN OXYGEN CONCENTRATION IN GASEOUS BODY WITH A PUMP CURRENT SUPPLY CIRCUIT AND AN AIR/FUEL RATIO CONTROL SYSTEM USING AN OXYGEN CONCENTRATION SENSING DEVICE

[75] Inventors: Tomohiko Kawanabe; Masahiko Asakura; Minoru Muroya; Katsuhiko Kimura; Noritaka Kushida; Hiroshi Hasebe, all of Wako, Japan

[73] Assignee: Honda Giken Kogyo Kabushiki Kaisha, Tokyo, Japan

[21] Appl. No.: 909,535

[22] Filed: Sep. 22, 1986

[30] Foreign Application Priority Data

Sep. 26, 1985 [JP] Japan ................................ 60-213577
Sep. 27, 1985 [JP] Japan ................................ 60-215788

[51] Int. Cl.⁴ ........................................... F02B 3/00
[52] U.S. Cl. .................................. 123/440; 123/489; 204/425
[58] Field of Search ............... 123/440, 489; 60/276; 204/424, 425, 426

[56] References Cited

U.S. PATENT DOCUMENTS 4,344,317  8/1982  Hahori ................................ 123/440
4,354,468 10/1980  Sone .................................. 123/489
4,359,030 11/1982  Sone .................................. 123/489
4,365,604 12/1982  Sone .................................. 123/440
4,548,179 10/1985  Ninomiya ........................... 123/440

Primary Examiner—Ronald B. Cox
Attorney, Agent, or Firm—Pollock, Vande Sande and Priddy

[57] ABSTRACT

An oxygen concentration sensing device and an air/fuel ratio control system for an internal combustion engine which include a pair of solid electrolyte members having oxygen ion permeability which are arranged to face each other to form a restricted region between them. One of the solid electrolyte members is operative as an oxygen pump element when a pump current is supplied across the electrodes thereof. The sensing device is provided with a current supply part including a limit command circuit which generates a current stop command signal when the magnitude of the pump current exceeds a reference limit level. With the current stop command signal, the supply of the pump current is stopped so as to prevent an overcurrent to the oxygen pump element. The air/fuel ratio control system includes an air/fuel ratio detection part and an air/fuel ratio control part operated by an air/fuel ratio detection signal. The detection of the air/fuel ratio and the supply of the pump current are stopped under a predetermined operating condition of the engine.

4 Claims, 9 Drawing Figures

FIG.1
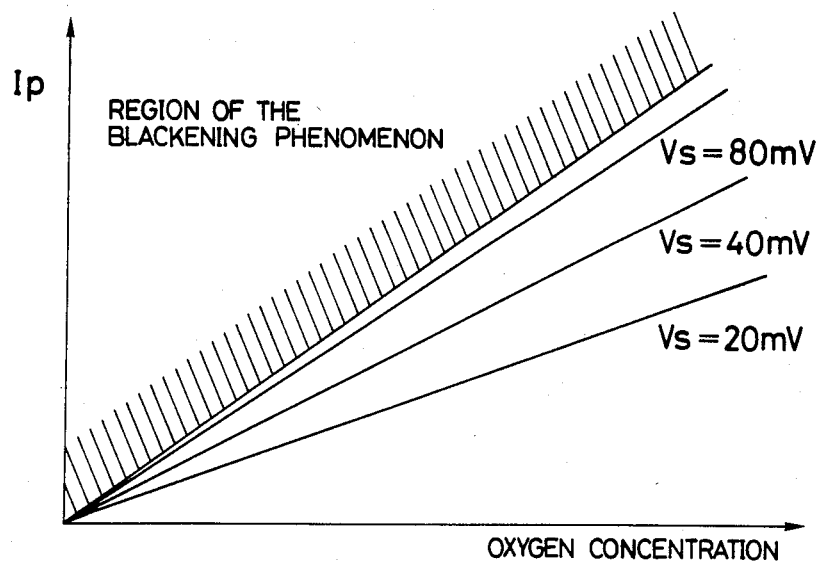
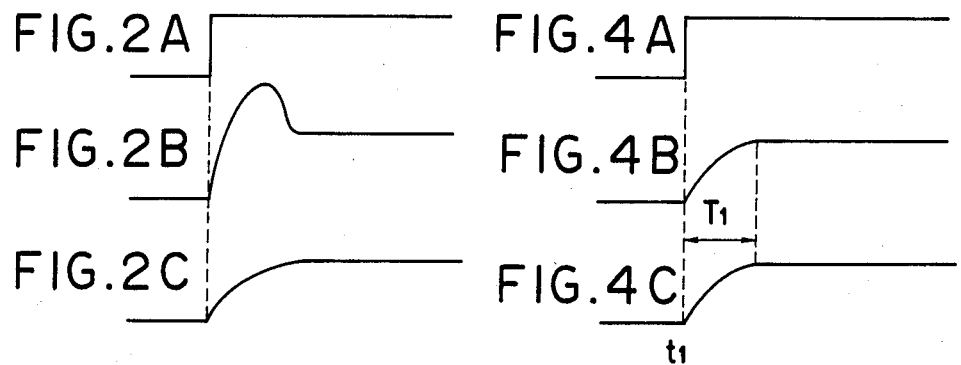

DEVICE FOR SENSING AN OXYGEN CONCENTRATION IN GASEOUS BODY WITH A PUMP CURRENT SUPPLY CIRCUIT AND AN AIR/FUEL RATIO CONTROL SYSTEM USING AN OXYGEN CONCENTRATION SENSING DEVICE

BACKGROUND OF THE INVENTION

1. Field of the Invention

The present invention relates to a device for sensing an oxygen concentration in a gaseous body, such as an exhaust gas of an internal combustion engine, and also relates to an air/fuel ratio feedback control system using an oxygen concentration sensing device.

2. Description of Background Information

Air-fuel ratio feedback control systems for an internal combustion engine are becoming generally used, which are constructed such that the oxygen concentration in the exhaust gas of the engine is detected by an oxygen concentration sensor and an air-fuel ratio of a mixture to be supplied to the engine is feedback controlled in response to a result of the detection of the oxygen concentration so as to purify the exhaust gas and improve the fuel economy.

As an example of oxygen concentration sensing device for use in the air-fuel ratio control system of the above mentioned type, an oxygen concentration sensing device having an output signal whose level is proportional to the oxygen concentration in a measuring gas (whose oxygen concentration is to be measured) is described in Japanese patent application laid open No. 58-153155. This oxygen concentration sensing device has a sensor element which has general construction including a pair of flat solid electrolyte members having oxygen ion permeability. These oxygen-ion conductive solid electrolyte members operative as active plates are placed in the atmosphere of the oxygen-containing measuring gas. Further, two electrodes are provided on the front and back surfaces of both of the solid electrolyte members. In other words, each pair of electrodes sandwich each solid electrolyte member. These two solid electrolyte members each having a pair of electrodes are arranged in face to face relation with each other to form a gap portion, or in other words, a restricted region between them.

With this arrangement, one of the solid electrolyte members serves as an oxygen pump element and the other one of the solid electrolyte members serves as a sensor cell element for sensing an oxygen concentration ratio. In the atmosphere of the mesuring gas, a drive current is supplied across the electrodes of the oxygen pump element in such a manner that the electrode facing the gap portion is used as a negative electrode. By the supply of this current, the oxygen component of the gas within the gap portion is ionized on the surface of the negative electrode of the solid electrolyte member operating as the oxygen pump element. The oxygen ions migrate through the inside of the oxygen pump element to the positive electrode, where the oxygen ions are released from the surface of the positive electrode in the form of the oxygen gas.

While this movement of oxygen ions is taking place, a voltage is generated across the electrodes of the solid electrolyte member operating as the sensor cell element because the oxygen concentration is different for the gas in the gap portion and the gas outside the electrodes of the sensor cell element. This difference of the oxygen concentration is caused by a reduction of the oxygen gas component within the gap portion. Then, if the magnitude of the electric current supplied to the sensor cell element is varied so as to maintain the voltage across the sensor cell element, the magnitude of the electric current varies substantially linearly in proportion to the oxygen concentration of the test gas at a constant temperature.

In this type of oxygen concentration sensing devices, if an excessive current is supplied to the oxygen pump element, it causes the so called blackening phenomenon by which the oxygen ions are removed from the solid electrolyte members. For instance, when zirconium dioxide ($ZrO_2$) is utilized as the solid electrolyte, the oxygen ions $O_2$ are removed from the zirconium dioxide ($ZrO_2$) so that zirconium (Zr) is separated out. As a result of this blackening phenomenon, deterioration of the oxygen pump element takes place rapidly, to cause a debasement of an operation of the oxygen concentration sensing device as a whole.

FIG. 1 shows curves indicating the relationship between the oxygen concentration and the magnitude of the pump current supplied to the oxygen pump element for different values of the voltage Vs generated by the sensor cell element which is expressed as a parameter. A region of occurence of the blackening phenomenon is also illustrated in FIG. 1. The boundary of the region of blackening phenomenon is, like the curves of the pump current which is expressed by using the parameter of the voltage of the sensor cell element Vs, on a curve linearly increases with respect to the oxygen concentration. This means, whether or not the magnitude of the current supplied to the oxygen pump element is in the region of blackening phenomenon is determined by means of the voltage Vs generated by the sensor cell element. Therefore, it can be assumed that magnitude of the current supplied to the oxygen pump element approaches to the region of the blackening phenomenon when the voltage Vs is higher than a predetermined level, and the occurence of the blackening phenomenon can be prevented by reducing the current to the oxygen pump element.

In air/fuel ratio control systems using this type of oxygen concentration sensing device, magnitude of the current to be supplied to the oxygen pump element is set at a level below a critical level of the occurence of the blackening phenomenon in order to prevent the said phenomenon. Therefore, by comparing the output signal level of the oxygen concentration sensing device with a reference voltage, detection is performed as to whether the air/fuel ratio of mixture is on the rich side or the lean side with respect to the target air fuel ratio. If the air/fuel ratio control system is of the type in which the air/fuel ratio is controlled by the supply of the secondary air, the secondary air is supplied when the rich air/fuel ratio is detected, and the supply of the secondary air is stopped when the lean air/fuel ratio is detected. In this way, the air/fuel ratio of mixture to be supplied to the engine is controlled toward the target air/fuel ratio.

The feedback control of the air/fuel ratio may be stopped in response to operating conditions of the engine. For instance, when the engine load is high, or when the engine coolant temperature is low, it is general to stop the feedback control of the air/fuel ratio. The air/fuel ratio may be enriched, for example by a fuel increasing system, when the feedback control of the air/fuel ratio is stopped. In such a period in which the feedback control is stopped, a critical level of the occurence of the blackening phenomenon reduces as the air/fuel ratio becomes rich. Therefore, the blackening phenomenon inevitably occurs unless the supply of the pump current is stopped in such a period.

On the other hand, for supplying the current to the oxygen pump element, there is a current supply circuit in which the magnitude of the current to the oxygen pump element is controlled in response to a result of a comparison between the voltage generated by the sensor cell element and a reference voltage.

FIGS. 2A and 2B show the variation of the control voltage supplied to the constant current circuit and the corresponding variation of the current supplied to the oxygen pump element in a conventional arrangement. As shown in FIG. 2A, when the supply of the control voltage to the constant current circuit is initiated, for instance, at the time of start of the engine, the constant current circuit starts to supply the pump current to the oxygen pump element. However, due to a delay of response of the air/fuel ratio control system, the pump current does not reach a desired constant level immediately. Instead, as shown in FIG. 2B, an overshoot of the pump current occurs during a transitional period. Therefore, the magnitude of the pump current exceeds the critical level of the occurence of the blackening phenomenon so that the blackening phenomenon may actually take place.

In the other aspect, because of the presence of the gap portion between the oxygen pump element and the sensor cell element, delay of response of the sensor cell element inevitably arises. Particularly, the level of the output signal does not increase and reach the reference voltage immediately, even the pump current to the oxygen pump element has risen above the constant current value corresponding to the reference current value after the start of the supply of the pump current. Instead, the output signal level increases gradually as illustrated in FIG. 2C.

For this reason, although the output signal level of the sensor cell element is monitored for detecting an overcurrent flowing through the oxygen pump element in some systems, it has been difficult to prevent the generation of an overcurrent immediately after the start of the supply of the pump current to the oxygen pump element.

OBJECT AND SUMMARY OF THE INVENTION

An object of the present ivention is therefore to provide an oxygen concentration sensing device by which the blackening phenomenon is surely prevented even immediately after the start of the supply of the pump current.

Another object of the present invention is to provide an air/fuel ratio control system in which the blackning phenomenon is surely prevented even immediately after the stop of the feedback control of the air/fuel ratio and immediately after the start of the supply of the pump current.

According to the present invention, the oxygen concentration sensing device is provided with a current supply unit including a limit command circuit which generates a current stop command signal when the magnitude of the pump current exceeds a reference limit value, a control voltage generator, a charge and discharge circuit normally charged by the control voltage and operative to discharge its electric charge upon receipt of the current stop command signal, and a current supply circuit for supplying the pump current across the electrodes of the oxygen pump element so that a voltage across the electrodes of the oxygen pump element becomes equal to a voltage of an output signal of the charge and discharge circuit.

According to another aspect of the invention, an air/fuel ratio control system for an internal combustion engine includes a control voltage generator for generating a control voltage, a charge and discharge circuit normally charged by the control voltage and operative to discharge its electric charge during a predetermined operating state of the engine, a current supply circuit connected to the charge and discharge circuit, for supplying a pump current to an oxygen pump element of an oxygen concentration sensing device so that the voltage across electrodes of the oxygen pump element is equal to a voltage of an output signal of the charge and discharge circuit and the pump current is stopped during the predetermined operating state of the engine.

BRIEF EXPLANATION OF THE DRAWINGS

FIG. 1 is a diagram showing a relation between the oxygen concentration in the exhaust gas and the magnitude of the pump current, and a region of occurence of the blackening phenomenon;

FIGS. 2A through 2C are waveform diagrams showing the operation of a conventional oxygen concentration sensing device;

FIGS. 4A through 4C are waveform diagrams similar to FIGS 1A through 1C, showing the operation of the oxygen concentration sensing device illustrated in FIG. 3.

DETAILED DESCRIPTION OF THE PREFERRED EMBODIMENTS

Figure 3:
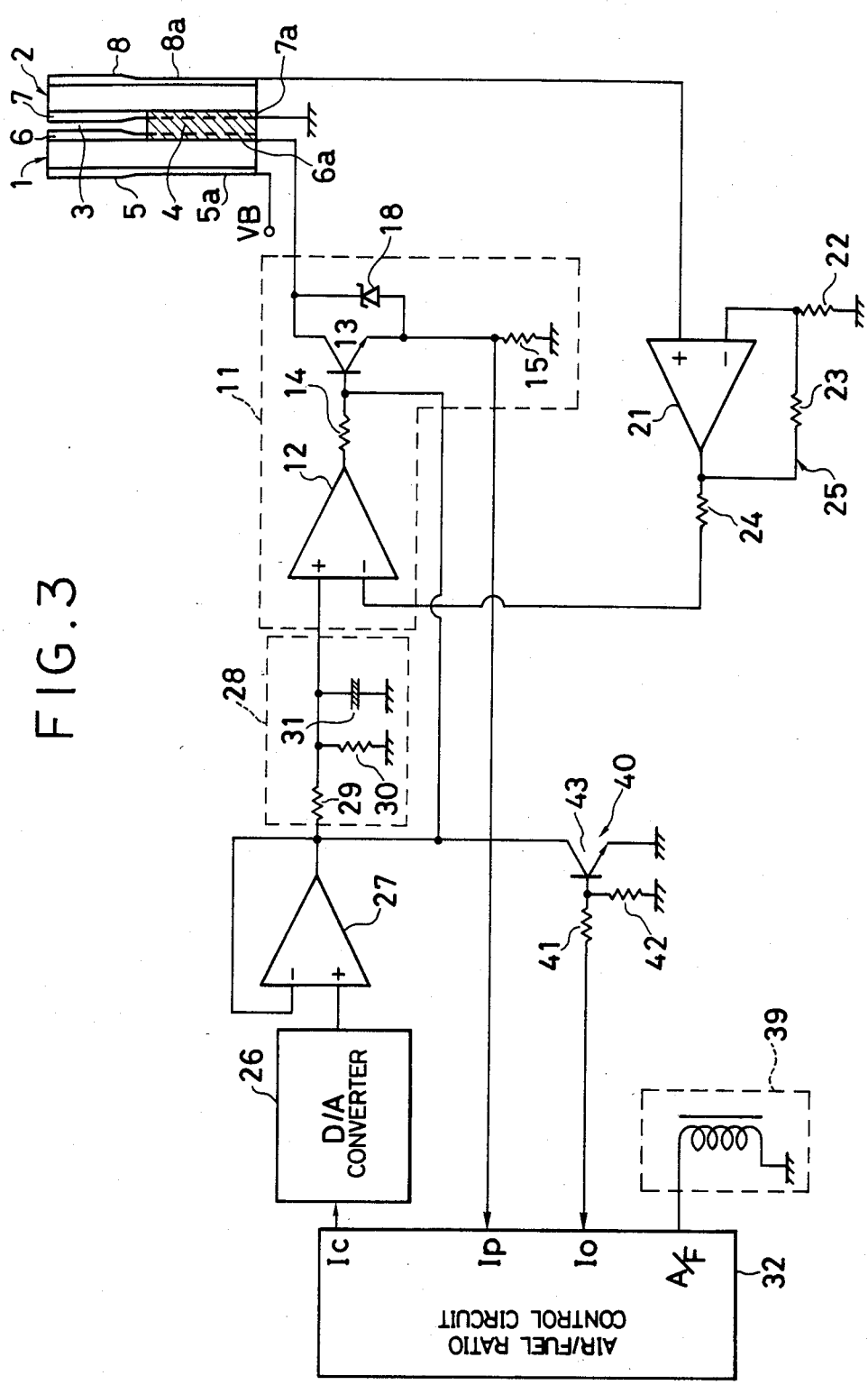
FIG. 3 is a block diagram showing an embodiment of an oxygen concentration sensing device and an air/fuel ratio control system according to the present invention.

FIG. 3 shows an example of air/fuel ratio control system in which the oxygen concentration sensing device according to the present invention is utilized. In this system, the oxygen concentration sensing device which is made up of a pair of elements, namely an oxygen pump element 1 and a sensor cell element 2 arranged in parallel to each other is mounted in an exhaust pipe (not shown) of an internal combustion engine. The main portions of the oxygen pump element 1 and the sensor cell element 2, i.e. first and second active plates, are made of an oxygen-ion conductive solid electrolyte member. An end portion of the oxygen pump element 1 and an end portion of the sensor cell element 2 which face each other are spaced apart so as to form a gap portion (or a restricted region) 3 between them. The other end portions of the oxygen pump element 1 and the sensor cell element 2 are connected to each other by means of a spacer 4. The oxygen pump element 1 and the sensor cell element 2 are provided, at their free end portions and on both sides thereof, with square electrodes 5 through 8 which are made of a porous heat-proof metal. Further, lead wires 5a through 8a of the square electrodes 5 through 8 respectively, are provided on both surfaces of the connected end portions of the oxygen pump element 1 and the sensor cell element 2. The square electrodes 6 and 7 are located in the inner sides of the oxygen pump element 1 and the sensor cell element 2 facing the gap portion 3. Therefore, they are also referred to as inner electrodes. Similarly, the square electrodes 5 and 8 located in the outer sides of the oxygen pump element 1 and the sensor cell element 2 are also referred to as outer electrodes.

Across the electrodes 5 and 6 of the oxygen pump element 1, a constant current is supplied from a constant current source 11. The constant current source 11 is made up of an operational amplifier 12, an NPN transistor 13, and resistors 14 and 15. More particularly, an output terminal of the operational amplifier 12 is connected to the base of the transistor 13 via the resistor 14. The emitter of the transistor 13 is connected to the ground via the resistor 15. The resistor 15 is provided to detect the magnitude of the pump current $I_P$ flowing between the electrodes 5 and 6 of the oxygen pump element 1. A voltage across the terminals of the resistor 15 is supplied to an $I_P$ input terminal of an air/fuel ratio control circuit 32 as a signal indicative of the magnitude of the pump current. The collector of the transistor 13 is connected to the inner electrode 6 of the oxygen pump element 1 through the lead wire 6a. The outer electrode 5 of the oxygen pump element 1 is supplied with an electric current having a voltage $V_B$ through the lead wire 5a. A zener diode 18 is connected between the collector and the emitter of the transistor 13 so that its cathode is connected to the collector of the transitor 13. This zener diode 18 is provided so as to prevent an application of an overvoltage (a voltage higher than the withstand voltage of the transistor 13) across the collector and the emitter of the transistor 13.

On the other hand, the inner electrode 7 of the sensor cell element 2 is grounded through the lead wire 7a, and the outer electrode 8 of the sensor cell element 2 is connected, through the lead wire 8a, to a noninverting amplifier 25 which is made up of an operational amplifier 21 and resistors 22 through 24. An output terminal of the noninverting amplifier 25 is connected to an inverting input terminal of the operational amplifier 12. An $I_c$ control output terminal of the air/fuel ratio control circuit 32 is connected to a D/A converter 26 which, in turn, generates a votage corresponding to Vs value command data provided at the Ic control output terminal of the air/fuel ratio control circuit 32. The output terminal of the D/A convertor 26 is connected to an integration circuit 28 through a voltage follower circuit 27. The integration circuit 28 is made up of resistors 29 and 30 and a capacitor 31, and whose output signal is supplied to a noninverting input terminal of the operational amplifier 12. Therefore, the integration circuit 28 may be referred to as a charge and discharge circuit 28.

The air/fuel ratio control circuit 32 preferably comprises a microcomputer, and has an A/F drive terminal and an Io output terminal in addition to the above mentioned Ic output terminal and $I_P$ input terminal. A solenoid valve 39 for controlling the amount of the secondary air is connected to the A/F drive terminal. The solenoid valve 39 is provided in an air intake side secondary air supply passage which connects to an intake air passage of the engine, at a position downstream of the throttle valve of a carburettor. To the Io output terminal of the air/fuel ratio control circuit 32, there is connected a switch circuit 40 which is made up of resistors 41 and 42, and a transistor 43. The transistor 43 turns on when a current stop command is supplied from the Io output terminal of the air/fuel ratio control circuit 32. By the conduction of the transistor 43, an input line of the integration circuit 28 at the terminal of the resistor 29 and the base of the transistor 13 are short-circuited to the ground.

With this circuit construction, when the Vs value command data are supplied from the Ic control terminal of the air/fuel ratio control circuit 32 to the D/A converter 26 at a point of time $t_1$, the Vs value command data are converted to a control voltage Vc at the D/A converter 26, and in turn supplied to the integration circuit 28 through the voltage follower circuit 27 as illustrated in FIG. 4A. As shown in FIG. 4B, the output signal level of the integration circuit 28 increases gradually due to the presence of an integration time constant determined by the resistors 29 and 30 and the capacitor 31. In this way, the level of the output signal of the integration circuit 28 reaches a divided voltage of the control voltage Vc by the resistors 29 and 30 after the elapse of a predetermined time period $T_1$ from the point of time $t_1$. The divided voltage thus obtained is in turn supplied to the noninverting input terminal of the operational amplifier 12 as an integration output voltage $V_{r1}$. Since the voltage level of the inverting input terminal of the operational amplifier 12 is lower than the integration output voltage $V_{r1}$, the operational amplifier 12 produces a high level output signal. Therefore, the transistor 13 turns on, so that the pump current flows between the electrodes 5 and 6 of the oxygen pump element 1.

As the flow of the pump current, a voltage Vs appears across the electrodes 7 and 8 of the sensor cell element 2. As shown in FIG. 4C, from the point of time $t_1$, this voltage Vs gradually goes up, to approach a predetermined voltage level after the elapse of a predetermined time period $T_1$ from the point of time $t_1$. This voltage Vs is amplified by the noninverting amplifier 25, which in turn supplies the amplified voltage to the inverting input terminal of the operational amplifier 12. When the voltage Vs rises, the output signal Vs' of the noninverting amplifier 25 also goes up. If the voltage Vs' becomes higher than the integration output voltage $V_{r1}$, the output signal of the operational amplifier 12 becomes low, to turn off the transistor 13. As the transistor 13 turns off, the pump current decreases to reduce the voltage Vs appearing across the electrodes 7 and 8 of the sensor cell element 2. As a result, the voltage Vs' from the non-inverting amplifier 25 supplied to the inverting input terminal of the operational amplifier 12 decreases. When the voltage Vs' becomes lower than the integration output voltage $V_{r1}$, the output signal of the operational amplifier 12 turns to the high level, to increase the pump current. Since these operations are repeated at a high speed, the voltage Vs is controlled to a constant value, and it becomes equal to a voltage corresponding to a value indicated by the Vs value command data.

The magnitude of the pump current $I_P$ flowing through the electrodes 5 and 6 of the integration output voltage when the integration output voltage $V_{r1}$ is supplied to the operational amplifier 12, is detected by means of a terminal voltate $V_p$ of the resistor 15, and the ternal voltage $V_P$ is supplied to the $I_P$ input terminal of the air/fuel ratio control circuit 32.

Figure 5:
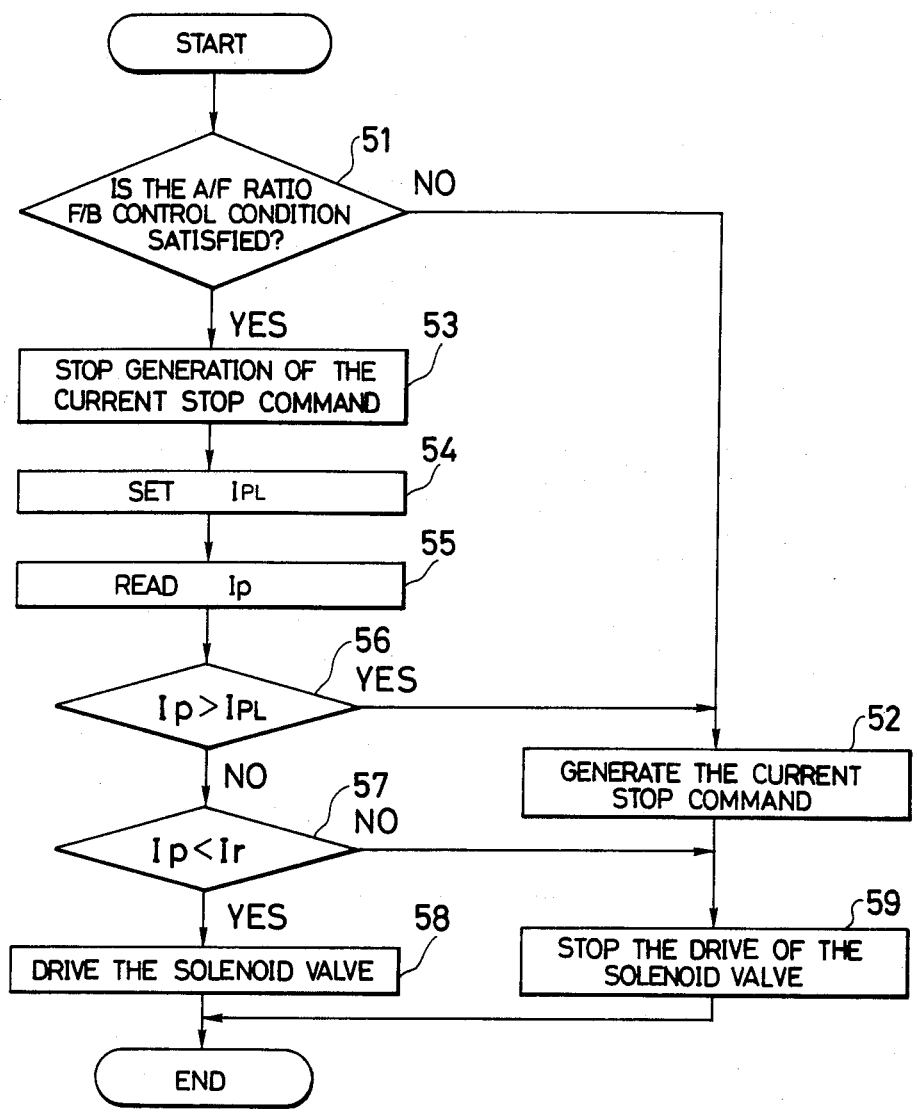
FIG. 5 is a flow chart showing the manner of operation of the control circuit in the device and the system of the present invention shown in FIG. 3.

In synchronizm with the rotation of the engine, the air/fuel ratio control circuit 32 operates as follows. As shown in FIG. 5, whether or not a condition for the feedback (F/B) control of the air/fuel ratio is detected first at a step 51. This detection is performed by using various engine parameters such as the engine speed, the intake manifold pressure, and the engine cooling water temperature. In addtion, for sensing these engine parameters, a plurality of sensors (not shown) are provided. When the condition of the feedback control is not satisfied, for example, when the engine load is high or when the engine cooling water temperature is low, the air/fuel ratio of the mixture supplied to the engine is enriched from a stoichiometric air/fuel ratio. Under this condition, a current stop command which consists of a high level signal is supplied from the air/fuel ratio control circuit 32 to the switch circuit 40 at a step 52. In response to the current stop command, the transistor 43 of the switch circuit 40 turns on, to reduce the voltage of the base of the transistor 13 to the ground level. Thus, the transistor 13 turns off to stop the supply of the pump current across the electrodes 5 and 6 of the oxygen pump element 1. At the same time, the voltage level of the input line of the integration circuit 28 from the voltage follower circuit 27 is made equal to the ground level. Thus, a current flows from the capacitor 31 to the ground through the resistors 29 and 30. In this way, the capacitor 31 is discharged to gradually reduce the voltage of the output signal of the integration circuit 28.

On the other hand, if the condition for the feedback control of the air/fuel ratio is satisfied, the generation of the current stop command is stopped at a step 53. By the stop of the generation of the current stop command, the transistor 43 turns off, to supply the voltage from the voltage follower circuit 27 to the integration circuit 28. The capacitor 31 is thus charged so that the voltage at the terminal of the capacitor, i.e. the voltage of the output signal of the integration circuit 28 increases gradually. As the transistor 43 turns off, the base of the transistor 13 is released from the ground level. Therefore, the current supply circuit 11 including this transistor 13 supplies the pump current to the electrodes of the pump element 1 in accordance with the output voltage of the integration circuit 28. The pump current $I_P$ thus increases rapidly to a level corresponding to the output voltage of the integration circuit 28 after the stop of generation of the current stop command. Subsequently, the pump current $I_P$ gradually increases with time. Moreover, if the operation of this step 53 has been executed at least once after the condition of the feedback control of the air/fuel ratio was satisfied, the step 53 can be ignored until the condition of the feedback control of the air/fuel ratio is no more satisfied. Then, a limit value $I_{PL}$ of the pump current corresponding to a current value of the target air/fuel ratio is set at a step 54. The limit value $I_{PL}$ is, for example, looked up from a data map previously stored in a ROM incorporated in the air/fuel ratio control circuit 32. After the set of the limit value $I_{PL}$, the terminal voltage $V_P$ is read as the pump current value at a step 55. Then, whethere or not the read value of the pump current $I_P$ is larger than the limit value $I_{PL}$ at a step 56. If $I_P > I_{PL}$, there is a posibility of the occurence of the blackening phenomenon. Therefore, the operation of the step 52 is performed to stop the supply of the pump current $I_P$. If $I_P \leq I_{PL}$, whether or not the read value of the pump current $I_P$ is smaller than a reference value $I_r$ corresponding to the target air/fuel ratio at a step 57. IF $I_P < I_r$, it means that the air/fuel ratio of mixture supplied to the engine is rich, and the air/fuel ratio control circuit 32 drives the solenoid valve 39 to open at a step 58, so that the secondary air is supplied to the engine. If $I_P \geq I_r$, it means that the air/fuel ratio of mixture supplied to the engine is lean, and the air/fuel ratio control circuit 32 stops the driving of the solenoid valve 39 at a step 59, so as to stop the supply of the secondary air to the engine. Further, during the operation of the step 52, the operation of the step 59 is also performed to stop the supply of the secondary air to the engine.

It will be appreciated from the foregoing, according to the present invention the oxygen concentration sensing device is constructed to stop the supply of the pump current to the oxygen pump element when the pump current value is greater than the limit value. Therefore, the blackening phenomenon can be surely prevented even though there is a time lag before the detection of a result of the air/fuel ratio control by means of the secondary air is detected by means of the oxygen concentration in the exhaust gas. Further, since the magnitude of the pump current increases gradually after the start of the supply of the pump current to the oxygen pump element, the pump current is prevented from entering into a region of the occurence of the blackeneing phenomenon even through there is a delay of response of the operation for preventing the supply of an excessive pump current, which delay is caused by the presence of the gap portion between the oxygen pump element and the sensor cell element.

Moreover, in the air/fuel ratio control system according to the present invention, the supply of the pump current to the oxygen pump element is stopped immediately upon occurence of an operating condition of the engine in which the feedback control of the air/fuel ratio is to be stopped. Therefore, the occurence of the blackening phenomenon is surely prevented even if the air/fuel ratio is enriched by a fuel increasing system when the feedback control of the air/fuel ratio is stopped. Further, since the pump current increases gradually after the start of the supply of the pump current to the oxygen pump element, the pump current is prevented from entering into the region of the blackening phenomenon. Thus, the blackening phenomenon is prevented even if there is a delay of an overcurrent limiting operation, for example by a limiter circuit, because of the presence of the gap portion or the restricted region between the oxygen pump element and the sensor cell element.

So far, an embodiment of the present invention has been described by way of example of an air/fuel ratio cotnrol system in which the amount of the air intake side secondary air is controlled. However, it is to be noted that the application of the present invention is not limited to this, and for example, the present invention is applicable to an air/fuel ratio control system which is arranged to control the fuel supply amount.

What is claimed is:

1. An oxygen concentration sensing device comprising:

an oxygen sensing unit being sensitive to oxygen in an oxygen-containing gas and operative to produce an output signal having a magnitude proportional to the concentration of oxygen in the oxygen-containing gas when contacted by a stream of the gas and having a sensor cell element made of a first active plate of an oxygen-ion conductive solid electrolyte and a first pair of electrodes sandwiching said active plate, an oxygen pump element made of a second active plate of an oxygen-ion conductive solid electrolyte and a second pair of electrodes sandwiching said active plate, said first and second active plates confronting a restricted region into which said oxygen-containing gas is introduced; and current supply part connected to said oxygen pump element for supplying a pump current across the electrodes of said oxygen pump element, wherein a magnitude of said pump current indicates an oxygen concentration of said oxygen-containing gas, said current supply part includes limit command means for generating a current stop command signal when said magnitude of said pump current exceeds a predetermined reference limit value, control voltage generating means for generating a control voltage, a charge and discharge circuit connected to said limit command means and said control voltage generating means, normally charged by said control voltage and operative to discharge its electric charge in response to said current stop command signal, and a current supply circuit connected to said charge and discharge circuit, for supplying said pump current across the electrodes of said oxygen pump element so that a voltage across said electrodes of said oxygen pump element becomes equal to a voltage of an output signal of the charge and discharge circuit.

2. A device as set forth in claim 1, wherein said device is provided on an internal combustion engine having an air/fuel ratio control system, and wherein said reference limit value is varied in reponse to a variation of a target air/fuel ratio of said air/fuel ratio control system.

3. An air/fuel ratio control system for an internal combustion engine having an exhaust gas passage, comprising:

an oxygen sensing unit disposed in said exhaust gas passage, and operative to produce an output signal having a magnitude proportional to the concentration of oxygen in an exhaust gas of an internal combustion engine and having a sensor cell element made of a first active plate of an oxygen-ion conductive solid electrolyte and a first pair of electrodes sandwiching said active plate, an oxygen pump element made of a second active plate of an oxygen-ion conductive solid electrolyte and a second pair of electrodes sandwiching said active plate, said first and second active plates confronting a restricted region into which said exhaust gas is introduced; and current supply means connected to said oxygen pump element for supplying a pump current across the electrodes of said oxygen pump element;

engine operation detection means for detecting a predetermined state of engine operation and producing an engine operation detection signal;

air/fuel ratio detection means connected to said current supply means and said engine operation detection means, for detecting an air/fuel ratio of a mixture supplied to said internal combustion engine in response to a magnitude of said pump current supplied from said current supply means, stopping the detection upon presence of said engine operation detection signal; and air/fuel ratio control means connected to said air/fuel ratio detection means, for controlling the air/fuel ratio of the mixture supplied to the engine in response to a result of detection of the air/fuel ratio by said air/fuel ratio detection means, wherein said current supply means includes a control voltage generating means for generating a control voltage, a charge and discharge circuit connected to said engine operation detection means and said control voltage generating means, normally charged by said control voltage and operative to discharge its electric charge in response to said engine operation detection signal, and a current supply circuit connected to said charge and discharge circuit, for supplying said pump current across the electrodes of said oxygen pump element so that a voltage across said electrodes of said oxygen pump element becomes equal to a voltage of an output signal of the charge and discharge circuit.

4. A system as set forth in claim 3, wherein said predetermined state of engine operation is a state in which the air/fuel ratio of the mixture supplied to the engine is to be enriched from a stoichiometric air/fuel ratio.

* * * * *